United States Patent [19]
Askin et al.

[11] Patent Number: 5,929,243
[45] Date of Patent: Jul. 27, 1999

[54] PROCESS FOR THE PREPARATION OF (S)-3-CARBETHOXY-3-BENZYLPIPERIDINE

[75] Inventors: David Askin, Warren; Peter Maligres, Scotch Plains; Michel Chartrain, Westfield; Ralph Volante, Cranbury, all of N.J.

[73] Assignee: Merck & Co., Inc., Rahway, N.J.

[21] Appl. No.: 09/053,812

[22] Filed: Apr. 2, 1998

Related U.S. Application Data

[60] Provisional application No. 60/043,231, Apr. 10, 1997.

[51] Int. Cl.$^6$ .................................................. C07D 211/60
[52] U.S. Cl. ............................................................ 546/227
[58] Field of Search ............................................... 546/227

[56] References Cited

U.S. PATENT DOCUMENTS 5,492,916  2/1996  Morriello et al. ....................... 514/318

OTHER PUBLICATIONS

Chem. Abstracts vol. 122 No. 314458, Naruto et al, "Preparation of 4–piperidinylalkenoylbenzene derivatives", Apr. 1994.

*Primary Examiner*—Alan L. Rotman
*Assistant Examiner*—Raymond Covington
*Attorney, Agent, or Firm*—J. Eric Thies; David L. Rose

[57] ABSTRACT

The present invention is concerned with a novel process for the preparation of a compound of the formula:

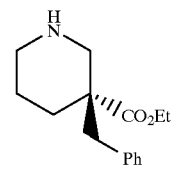

This compound is useful as an intermediate in the synthesis of compounds which possess pharmacological activity.

26 Claims, No Drawings

PROCESS FOR THE PREPARATION OF (S)-3-CARBETHOXY-3-BENZYLPIPERIDINE

CROSS REFERENCE TO RELATED APPLICATIONS

This application claims priority under 35 U.S.C. § 119(e) from U.S. application Ser. No. 60/043,231, filed Apr. 10, 1997.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low.

Certain trisubstituted piperidine compounds are disclosed in U.S. Pat. No. 5,492,916 (issued Feb. 20, 1996) as being non-peptidal growth hormone secretagogues. These compounds have the ability to stimulate the release of natural or endogenous growth hormone and thus may be used to treat conditions which require the stimulation of growth hormone production or secretion such as in humans with a deficiency of natural growth hormone or in animals used for food or wool production where the stimulation of growth hormone will result in a larger, more productive animal.

Among the preferred compounds disclosed therein is the compound:

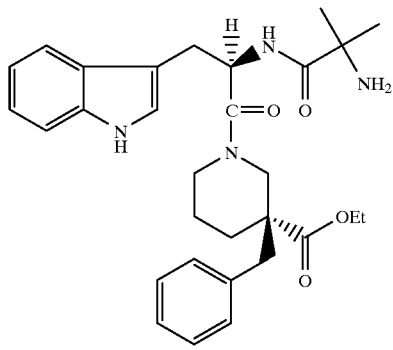

and pharmaceutically acceptable salts thereof, in particular, the hydrochloride salt. The processes for the preparation of this compound are described in U.S. Pat. No. 5,492,916 by Morriello et al. The processes described therein proceed by preparation of a racemic 3-benzylnipecotate followed by separation of the the enantiomers at some step of the overall process. The maximum theoretical yield of optically active product by such procedures is 50%.

In accordance with the present invention there is provided a process in which the S-piperidine intermediate [(S)-3-carbethoxy-3-benzylpiperidine]is prepared from optically active S-monoacid/ monoester which is obtained from the prochiral diester via an efficient esterase hydrolysis, thereby avoiding the drastic automatic loss of 50% of some intermediate. The problem with the previous procedure for the preparation of the piperidine intermediate is that a resolution of the corresponding tartrate salt via a crystallization is necessary to obtain optically active piperidine needed for the preparation of the final compound. The maximum theoretical yield of optically active material by such a procedure is 50%.

The advantage of the instant stereoselective hydrolysis procedure is that it provides product of high optical activity (>99% ee) in high yield (80%). In contrast, for the resolution based procedure half of the material is lost as its antipode.

Some work on the enzymatic hydrolysis of disubstituted malonate diesters has been reported by Iriuchijima, *Agric. Biol. Chem.*, 46, 1907–1910 (1982); Bjorkling et al., *Tetrahedron* 41, 1347–1352 (1985); Bjorkling et al., *Bioorganic Chemistry*, 14, 176–181 (1986); Dejeso et al., *Tetrahedron Letters*, 31, 653–654 (1990); and Toone et al., *J. Am. Chem. Soc.*, 31, 653–654 (1990).

SUMMARY OF THE INVENTION

The present invention is concerned with novel processes for the preparation of a compound of the formula:

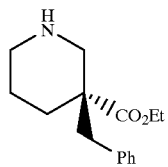

This compound is an intermediate in the synthesis of compounds which possess pharmacological activity. In particular, such compounds have the ability to stimulate the release of natural or endogenous growth hormone and may be used to treat conditions which require the stimulation of growth hormone production or secretion such as in humans with a deficiency of natural growth hormone or in animals used for food or wool production where the stimulation of growth hormone will result in a larger, more productive animal.

A key aspect of the novel process is provision of the optically active S-piperidine from a optically active S-monoacid/ monoester which is obtained from a prochiral diester via an efficient esterase hydrolysis which may be depicted as follows:

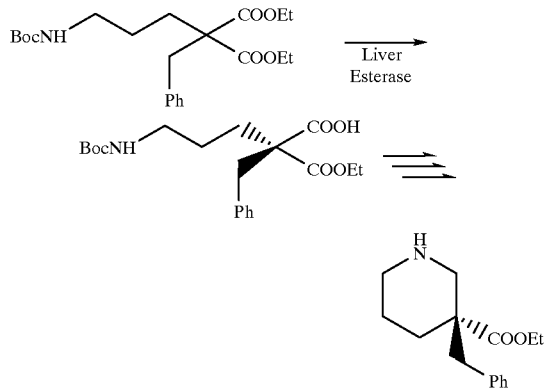

DETAILED DESCRIPTION OF THE INVENTION

The present invention is directed to processes for the preparation of a compound of the formula:

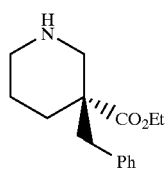

An embodiment of the present invention concerns a process for the preparation of a compound of the structural formula 5:

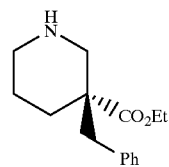

which comprises the steps of:
a) treating a compound of structural formula 1:

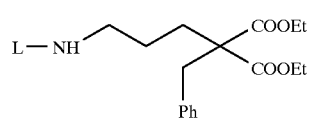

wherein L is an amino protecting group, with an esterase to give a compound of structural formula 2:

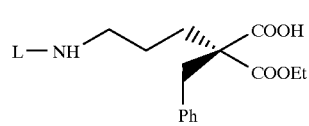

b) cyclizing the compound of structural formula 2 to give a compound of structural formula 3:

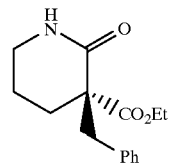

c) reducing the carbonyl of the compound of structural formula 3 to give the compound of structural formula 5.

Suitable amino protecting groups L include: benzyl, benzyloxymethyl, benzyloxycarbonyl (carbobenzyloxy), benzylsulfonyl, 2-bromo-ethyloxycarbonyl, t-butoxy-carbonyl, 2-chloro-benzyloxy-carbonyl, 2-chloroethyloxycarbonyl, di-t-amyloxycarbonyl, 9-fluoroenyl-methyloxycarbonyl, isopropoxycarbonyl, 4-methoxy-benzyloxycarbonyl, 4-nitrobenzyloxycarbonyl, 2-nitrophenyl-sulfonyl, phthaloyl, 2,2,2-trichloro-t-butyloxycarbonyl, trifluoroacetyl, triphenylmethane, allyloxycarbonyl, and vinyloxycarbonyl groups, and the like, in which the preferred ones include benzyloxycarbonyl (carbobenzyloxy), t-butoxy-carbonyl groups, and in which the most preferred one is the t-butoxy-carbonyl group.

In the present invention, the esterase may be any chemically functional esterase, but it is preferred that the esterase be a liver esterase, and more preferably a pig (porcine) or rabbit liver esterase. Suitable liver esterases are commercially available, including Sigme porcine liver esterase, Sigma rabbit liver esterase, and Boehringer Mannheim porcine liver esterase.

In the present invention, it is preferred that the treatment of the compound of formula 1 with an esterase is conducted in the presence of a gum, such as xanthan gum, locust bean gum, arabic gum, tragacanth gum, guar gum, elemi gum, or karaya gum. Preferred gums include xanthan gum, tragacanth gum, guar gum, elemi gum, and karaya gum, in which the more preferred gums are xanthan gum, tragacanth gum, and guar gum, and the most preferred gum is xanthan gum.

In the present invention, the cyclization to the piperidone intermediate is effected by removal of the amino protecting group. In this process, the removal of the amino protecting group may be accomplished by use of an appropriate catalytic agent. Removal of a t-butoxycarbonyl protecting group may be carried out in a solvent such as methanol, ethanol, methylene chloride, ethyl acetate, or iso-propyl acetate, with a strong acid. Such strong acids include methanesulfonic acid, trifluoroacetic acid, hydrochloric acid, hydrogen chloride gas, hydrogen bromide; hydrogen iodide; trifluoromethane-sulfonic acid; camphorsulfonic acid; sulfuric acid; phosphoric acid; and an arylsulfonic acid, such as benzenesulfonic acid, p-toluenesulfonic acid, and p-chlorobenzene-sulfonic acid. Preferred catalytic agents include: trifluoroacetic acid; hydrochloric acid; methanesulfonic acid; camphorsulfonic acid; benzenesulfonic acid; p-toluenesulfonic acid; and p-chlorobenzene-sulfonic acid. The most preferred catalytic agent is methanesulfonic acid or hydrochloric acid. The preferred solvent is methanol or ethanol, and the most preferred solvent is ethanol. The preferred reaction temperature range is between −40 and 150° C., and the most preferred range is between 10 and 40° C.

Following the removal of the amino protecting group, the cyclization proceeds by reaction with an activating agent in an inert solvent, optionally in the presence of a catalytic agent, to give the compound of formula 3.

Acid activating agents suitable for this process include: DCC, EDC, ECAC, BOP and 2-chloro-N-methylpyridinium iodide, in which the preferred acid activating agent is DCC (N,N'-dicyclohexyl-carbodiimide) or 2-chloro-N-methylpyridinium iodide. Catalytic agents suitable for this process include: HOBT, HONB, and the like in which a preferred catalytic agent is HOBT (hydroxybenzotriazole) or HONB (N-hydroxy-5-norbornene-2,3-dicarboximide). Inert solvents appropriate for this processes include: acetonitrile; isopropyl acetate; ethyl acetate; propionitrile; water; chlorinated hydrocarbons such as dichloromethane, chloroform, carbon tetrachloride, dichloroethane, chlorobenzene, ortho-dichlorobenzene; benzene; toluene; xylenes; and the like; and mixtures hereof, in which the preferred solvent is dichloromethane. The preferred reaction temperature range is between −40 and 150° C., and the most preferred range is between 10 and 40° C.

Conversion of the carbonyl in the compound of formula 3 to the alkane in the compound of formula 5 may be effected by reducing agents which are well known in the art. For example, the thiolactam may be prepared by reaction of the ketone with Lawesson's reagent. Inert solvents appropriate for this processes include: chlorinated hydrocarbons such as dichloromethane, chloroform, carbon tetrachloride, dichloroethane, chlorobenzene, ortho-dichlorobenzene; benzene; toluene; xylenes; tetrahydrofuran; dimethoxyethane; and the like; and mixtures thereof, in which the preferred solvent is dichloromethane. The preferred reaction temperature range is between −40 and 150° C., and the most preferred range is between 10 and 40° C. The thiolactam is then removed by reaction with Raney nickel. Inert solvents appropriate for this processes include: tetrahydrofuran; dimethoxyethane; methanol; or ethanol, where the most preferred solvent is tetrahydrofuran or ethanol. The preferred reaction temperature range is between −40 and 150° C., and the most preferred range is between 10 and 40° C.

Similarly, the carbonyl may be removed by first protecting the amino group with an amino protecting group by methods well known in the art. Suitable amino protecting groups include: benzyl, benzyloxymethyl, benzyloxycarbonyl (carbobenzyloxy), benzylsulfonyl, 2-bromo-ethyloxycarbonyl, t-butoxy-carbonyl, 2-chloro-benzyloxycarbonyl, 2-chloroethyloxycarbonyl, di-t-amyloxycarbonyl, 9-fluoroenyl-methyloxycarbonyl, isopropoxycarbonyl, 4-methoxy-benzyloxycarbonyl, 4-nitrobenzyloxycarbonyl, 2-nitrophenyl-sulfonyl, phthaloyl, 2,2,2-trichloro-t-butyloxycarbonyl, trifluoroacetyl, triphenylmethane, allyloxycarbonyl, and vinyloxycarbonyl groups, and the like, in which the preferred ones include benzyloxycarbonyl (carbobenzyloxy), t-butoxy-carbonyl groups, and in which the most preferred one is the t-butoxy-carbonyl group. The carbonyl is then reduced by treatment with a borane reducing agent, such as lithium triethyl borane (LiEt$_3$BH), followed by treatment with a silane, such as diethylsilane, in the presence of a Lewis acid, such as boron trifluoride etherate. The desired deprotected piperidine is then obtained by removal of the amino protecting group. In this process, the removal of the amino protecting group may be accomplished by use of an appropriate catalytic agent. Removal of a t-butoxycarbonyl protecting group may be carried out in a solvent such as methanol, ethanol, methylene chloride, ethyl acetate, or iso-propyl acetate, with a strong acid. Such strong acids include methanesulfonic acid, trifluoroacetic acid, hydrochloric acid, hydrogen chloride gas, hydrogen bromide; hydrogen iodide; trifluoromethane-sulfonic acid; camphorsulfonic acid; sulfuric acid; phosphoric acid; and an arylsulfonic acid, such as benzenesulfonic acid, p-toluenesulfonic acid, and p-chlorobenzene-sulfonic acid. Preferred catalytic agents include: trifluoroacetic acid; hydrochloric acid; methanesulfonic acid; camphorsulfonic acid; benzenesulfonic acid, p-toluenesulfonic acid; and p-chlorobenzene-sulfonic acid. The most preferred catalytic agent is methanesulfonic acid or hydrochloric acid. The preferred solvent is methanol or ethanol, and the most preferred solvent is ethanol. The preferred reaction temperature range is between −40 and 150° C., and the most preferred range is between 10 and 40° C.

Another embodiment within the present invention concerns a process for the preparation of a compound of the structural formula 5:

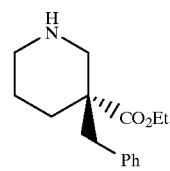

which comprises the steps of:

a) treating the compound of structural formula I:

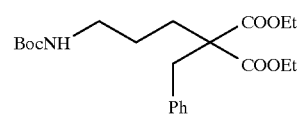

with a liver esterase to give the compound of structural formula 2:

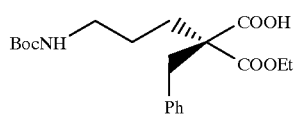

b) deprotecting the compound of structural formula 2 with trifluoracetic acid or hydrochloric acid followed by cyclization with dicyclohexylcarbodiimide and 1-hydroxybenzotriazole or 2-chloro-N-methylpyridinium iodide to give the compound of structural formula 3:

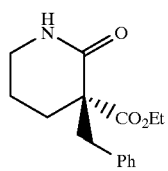

c) treating the compound of structural formula 3 with Lawesson's reagent to give the compound of structural formula 4:

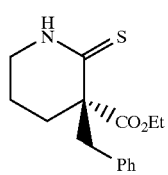

d) treating the compound of structural formula 4 with Raney nickel to give the compound of structural formula 5.

Another embodiment within the present invention concerns a process for the preparation of a compound of the structural formula 5:

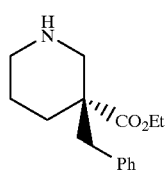

which comprises the steps of:

a) treating the compound of structural formula I:

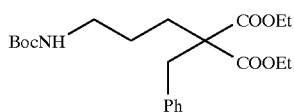

with a liver esterase to give the compound of structural formula 2:

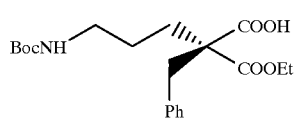

b) deprotecting the compound of structural formula 2 with hydrochloric acid, followed by cyclization with 2-chloro-N-methylpyridinium iodide to give the compound of structural formula 3:

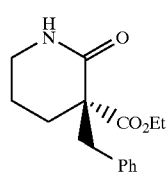

c) activating the compound of structural formula 3 as its Boc-derivative followed by reducing the carbonyl by sequential treatment with lithium triethyl borane (LiEt$_3$BH) and diethylsilane/boron trifluoride etherate and hydrolyzing of the Boc group with an acid to give the compound of structural formula 5.

The individual most preferred processes within the general process for the preparation of the chiral trisubstituted piperidine may be summarized as follows:

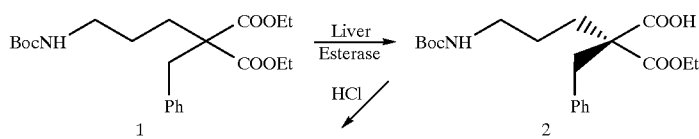

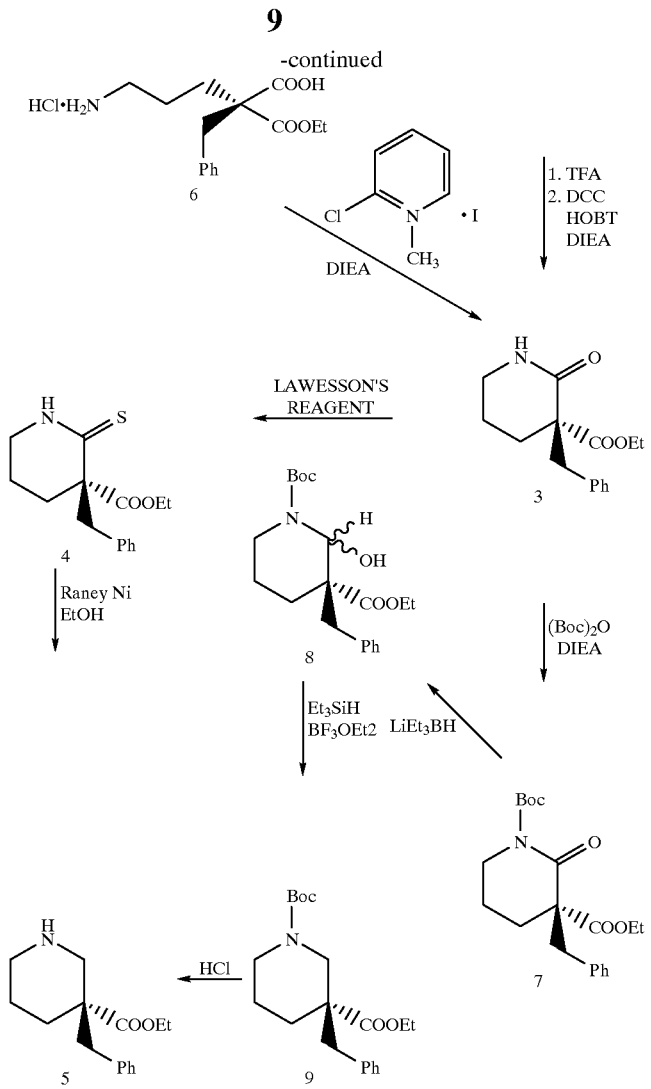

Enzymatic hydrolysis of diester 1 with an esterase, preferably a liver esterase and especially a pig or rabbit liver esterase, gives the monoacid 2 with a greater than 99% enantiomeric excess. It is preferred that the enzymatic hydrolysis be conducted in the presence of a gum, such as xanthan gum, locust bean gum, arabic gum, tragacanth gum, guar gum, elemi gum, or karaya gum, especially xanthan gum, tragacanth gum, or guar gum. The crude monoacid may be isolated as its crystalline complex with ½ mol of toluene. Monoacid 2 is converted to the lactam 3 by deprotection with trifluoroacetic acid (TFA) followed by ring closure under the influence of dicyclohexylcarbodiimide (DCC) and 1-hydroxybenzotriazole hydrate (HOBT) in the presence of a strong base such as diisopropyl ethylamine (DIEA), triethylamine, N-methyl-morpholine, pyridine, or dimethylaminopyridine. Treatment of 3 with Lawesson's reagent (2,4-bis(4-methoxyphenyl)-1,3-dithia-2,4-diphosphatane-2,4-disulfide) gives the thiolactam 4 which is reduced to the piperidine 5 with Raney nickle/ethanol.

An efficient route for the conversion of the enzymatic hydrolysis product 2 to S-piperidine 5 is also shown in the above scheme. Monoacid 2 is converted to the lactam 3 by Boc-deprotection with HCl and removal of volatiles followed by cyclization of crude 6 with 2-chloro-1-methylpyridinium iodide in an inert organic solvent such as a chlorinated alkane such as chloroform, methylene chloride, ethyl acetate toluene, or tetrahydrofuran to give the lactam 3. The lactam is then activated as its Boc-derivative 7 with Boc$_2$O and 4-dimethylamino-pyridine (DMAP) and reduced to the hemiaminal 8 with a reducing agent such as lithium triethyl borane (LiEt$_3$BH) in an ethereal solvent such as THF, diethyl ether, methyl t-butyl ether, dimethoxy ethane, or toluene. Further reduction to 5 is accomplished with triethyl silane (Et$_3$SiH) and boron trifluoride ether complex (BF$_3$•OEt$_2$) in a chlorinated hydrocarbon such as chloroform, methylene chloride or toluene followed by completion of the Boc-deprotection by passage of HCl into the reaction mixture. After extraction into water and converting to the free base, 5 is obtained in 85% yield from 8. This procedure gives the S-piperidine 5 in 61% overall yield and greater than 99% enantiomeric excess from 2 without isolation of any of the intermediates.

Although the details and the reagents may differ, the overall process of the present invention comprises the steps of: (1) esterase hydrolysis of the malonic acid diester to the enantiomeric pure half ester; (2) ring closure of the lactam; and (3) reduction of the carbonyl group.

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography.

The following examples are provided for the purpose of further illustration only and are not intended to be limitations on the disclosed invention.

EXAMPLE 1

(S)-3-Carbethoxy-3-benzylpiperidine

Step A: Benzyl-(2-cyanoethyl)-diethylmalonate

A solution of 21% NaOEt in EtOH (3 mL) was added to a solution of benzyl diethylmalonate (250.29 g, 1.00 mol), acrylonitrile (72.4 mL, 58.37 g, 1.10 mol), and methyl-t-butyl ether (MTBE) (100 mL) in a 500 mL flask equipped with a cold finger condenser filled with Dry ice/acetone. Within 5–10 min an exotherm was observed and the mixture began to reflux (10–15 min). The mixture was aged at 40° C. for 1 h. The mixture was diluted with 9:1 by vol MTBE-hexane (100 mL) and filtered through a pad of silica (15 g), washing the pad with 9:1 by vol MTBE-hexane (100 mL). The filtrate was evaporated to give benzyl-(2-cyanoethyl)-diethylmalonate (300.31 g, 99%). $^{13}$C NMR (62.9 MHz, CDCl$_3$) δ 170.5, 135.4, 130.3, 129.0, 127.9, 119.6, 62.3, 58.1, 40.0, 29.2, 14.4, 13.6.

Step B: Benzyl-(3-aminopropyl)-diethylmalonate HCl salt

The crude benzyl-(2-cyanoethyl)-diethylmalonate from above was dissolved in EtOH (1750 mL) and 5M aqueous HCl (250 mL, 1.25 mol). Pearlman's catalyst containing 20% palladium hydroxide (40 g) was added, and the mixture was hydrogenated in a 1 gallon Hastalloy vessel on a Parr shaker at 50° C. under 40 psi H$_2$ for 22 h. The slurry was filtered through a pad of solkafloc (100 g), and the pad was washed with EtOH (2000 mL). The filtrates were evaporated (25" Hg, bath at 100° C.), and the oily residue was dissolved in water (3500 mL). The aqueous solution was washed with 2:1 by vol hexane-MTBE (1000 mL), and the organic phase was extracted with water (500 mL). The combined aqueous phases were extracted with CH$_2$Cl$_2$ (3×500 mL). The organic extracts were dried over Na$_2$SO$_4$ and evaporated (100° C. at 10 Torr) to an oily residue which crystallized upon cooling to afford benzyl-(3-aminopropyl)-diethylmalonate HCl salt (240.0 g, 70%). $^1$H NMR (250 MHz, CD$_3$OD) δ 7.97 (br s, 1 H), 7.28–7.10 (m, 5 H), 4.19 (q,J=5.2 Hz, 4 H), 3.23 (s, 2 H), 3.01 (br s, 2 H), 1.90–1.73 (br m, 4 H), 1.23 (t,J=5.2 Hz, 4 H).

Step C: Benzyl-(3-N-Boc-aminopropyl)-diethylmalonate

To a solution of benzyl-(3-aminopropyl)-diethylmalonate HCl salt (100.0 g, 0.291 mol) in CH$_2$Cl$_2$ (600 mL) cooled to 10° C. was added Et$_3$N (6.6 mL, 4.8 g, 0.047 mol) followed by a solution of Boc$_2$O (65.5 g, 0.30 mol) and Et$_3$N (38 mL, 27.6 g, 0.27 mol) in CH$_2$Cl$_2$ (20 mL) added over 15 min. The temperature rose to 30° C. and was accompanied by gas evolution (CO$_2$). The mixture was aged for 2 h at 25° C. and was evaporated to a semi-solid/oil. The residue was diluted with MTBE (600 mL) and hexane (200 mL) and extracted with saturated aqueous NaH$_2$PO$_4$ (200 mL), 2:1 water-saturated aqueous NaH$_2$PO$_4$ (300 mL), water (500 mL) and saturated aqueous NaCl (200 mL). The organic phase was dried over MgSO$_4$ and filtered through a pad of silica (40 g), washing with 2:1 MTBE-hexane. The filtrates were concentrated to an oil and redissolved in hexane. The mixture was seeded with Boc carbamate D (10 mg), aged for 1 h, and hexane (600 mL) was added over 1 h. The mixture was gradually cooled to −20° C. over 26 h and filtered cold. The filter cake was washed with hexane (200 mL) at −30° C. and dried under a stream of nitrogen to give benzyl-(3-N-Boc-aminopropyl)-diethylmalonate (105 g, 89%) as a white crystalline solid. $^{13}$C NMR (62.9 MHz, CDCl$_3$) δ 171.1, 155.8, 136.0, 129.8, 127.0, 79.1. 61.3, 58.5, 40.5, 38.1, 29.1, 28.4, 24.8, 14.0.

Step D: (S)-2-Carbethoxy-2-benzyl-2-Boc-aminopentanoic acid (2)

In a Waring blender cup, were added: 50 ml of 200 mM Bis-Tris-propane buffer (Sigma) at pH 9.5, 400 mg of xanthan gum (final concentration 8 g/l), and 500 mg of benzyl-(3-N-Boc-aminopropyl)-diethylmalonate (final concentration 10 g/l) dissolved in 1 ml of ethanol. The mixture was blended for 2 minutes at high speed (Waring blender). An amount of 50 ml of the mixture was dispensed to 250-ml Erlenmeyer flasks and 6,250 units of porcine liver esterase (Sigma) were added to each flask. The flasks were incubated at 37° C. with shaking at 220 rpm. An ester acid 2 concentration of 8.24 g/l was achieved after 100 hours of incubation (yield of 82.4%). The enantiomeric excess of the produced material was 99%.

The crude residue from a 10 g run was dissolved in ethyl acetate (10 mL) and treated with MgSO$_4$ (0.4 g) and Darco G60 carbon (0.1 g) for 15 min at 25° C. The mixture was filtered through a pad of silica (3 g), washing with ethyl acetate (40 mL). The filtrates were evaporated to give 2 (9.64 g) as a pale yellow gum. The crude gum was dissolved in toluene (20 mL) at 60° C. Crystallization was initiated by seeding with crystalline 2 (2 mg) and completed by the slow addition of hexane (100 mL) over 2 h at 20° C. The slurry of crystalline mono acid solvate with ½ mol of toluene was filtered. The filter cake was washed with 5:1 hexane-toluene (30 mL) and hexane (2×30 mL) and dried to provide 2•½ toluene (6.1 g). Prolonged drying removed the remaining toluene from a 100 mg sample. 2: $^{13}$C NMR (62.9 MHz, CDCl$_3$) δ 174.6, 172.4, 156.1, 135.8, 129.7, 128.4, 127.1, 61.9, 58.6, 41.5, 40.4, 30.5, 28.4, 25.1, 14.0. HPLC analysis of the R-(+)-1-(napthyl)ethylamide derivative of 2 indicated >99.5 % ee.

Sample preparation for R-(+)-1-(napthyl)ethylamide derivatization: 0.5 mg monoacid 2, 0.5 mg R-(+)-(naphthyl) ethylamine, 0.5 mg EDC•HCl, 0.5 mg HOBT, and 0.1 mL acetontrile (MeCN) were combined. The mixture was heated at 55° C. (4–5 min.) and diluted to 1 mL with 1:1 MeCN and H$_{20}$. HPLC conditions: B-03-5 YMC Basic (S-5 micron) 250×4.6 mm column, isocratic elution over 10 min (42/58) MeCN/0.025% aq. H$_3$PO$_4$, then gradient elution over 5 min (42/58→62/38) MeCN/0.025% aq. H$_3$PO$_4$, then isocratic elution over 15 min (62/38) MeCN/0.025% aq. H$_3$PO$_{4, 1.0}$ mL/min flow at 25° C. with detection at 220 nm, retention times: R-(+)-1-(naphthyl)ethylamide derivative of (S)–2= 25.6 min, R-(+)-1-(naphthyl)ethylamide derivative of (R)– 13=26.2 min.

Step E: (S)-3-Carbethoxy-3-benzyl-2-piperidone (3)

A solution of Boc carbamate 2 (759 mg, 2.0 mmol) and TFA (764 mg, 6.70 mmol) in CH$_2$Cl$_1$ (3 g) was aged at 40° C. for 1.5 h. The volatiles were removed under a stream of nitrogen (40° C.), and the residue was dissolved in CH$_2$Cl$_2$ (3 g). DIEA (491 mg, 3.80 mmol), HOBT (41 mg, 0.30 mmol), DCC (516 mg, 2.5 mmol) and DMAP (12 mg, 0.10 mmol) were added sequentially, and the mixture was aged for 20 h at 25° C. Oxalic acid dihydrate (250 mg) and MTBE (5 mL) were added, and the mixture was aged for 1 h. The mixture was filtered from the dicyclohexyl urea (DCU), and the filter cake was washed with a mixture of CH$_2$Cl$_2$ (2 mL) and MTBE (15 mL). The filtrate was washed with saturated aqueous NaH$_2$PO$_4$ (2×10 mL), water (10 mL), saturated aqueous NaHCO$_3$ (10 mL), water (10 mL), and saturated aqueous NaCl (10 mL). The organic phase was dried over MgSO$_4$ and evaporated. The residue was purified by chromatography (silica, gradient elution, 10% MTBE in hexane then MTBE to provide piperidone 3 (366 mg, 70%).: $^{13}$C NMR (62.9 MHz, CDCl$_3$) δ 172.8, 170.5, 136.6, 130.6, 128.1, 126.6, 61.5, 54.8, 42.0, 40.5, 28.9, 19.5, 14.0. Chiral supercritical phase HPLC indicated 3 to be >99.5 % ee. HPLC conditions: Sumichiral AG OA3200 250×4.6 mm column, isocratic elution, 16% MeOH in supercritical CO$_2$ at 300 bar, 2.0 mL/min flow at 35° C. with detection at 210 nm. Retention times: (R)–3=2.35 min., (S)–3=2.87 min.

Step F: (S)-3-Carbethoxy-3-benzyl-piperidine (5)

A mixture of piperidone 3 (349 mg, 1.34 mmol) Lawesson's reagent (594 mg, 1.47 mmol) and toluene (1.5 mL) was heated to 110° C. for 2 h. The mixture was cooled to 25° C., aged for 15 min, and filtered through a cotton plug, washing with toluene (3.5 mL). The filtrate was evaporated, and the residue containing thiolactam 4 was dissolved in THF (2 mL) and EtOH (2 mL). A 50% aqueous slurry of Raney nickel (1 mL) was added. After a 5 min age another portion of the Raney nickel (1 mL) was added followed by NaBH$_4$ (25 mg). After 15 min the mixture was filtered through a pad of solkafloc, washing the pad with THF (5 mL) and EtOH (5 mL). The filtrates were evaporated to 4 mL and diluted with MTBE (20 mL). The mixture was extracted with 0.5M aqueous HCl (2×3 mL), and the aqueous extract was basified with 5M aqueous NaOH (0.7 mL). The aqueous mixture was extracted with CH$_2$Cl$_2$ (2×3 mL). The organic extracts were dried over Na$_2$SO$_4$ and evaporated to give piperidine 5 (100 mg, 30%) as a colorless oil: $^{13}$C NMR (62.9 MHz, CDCl$_3$) δ 175.1, 136.5, 129.6, 127.8, 126.4, 60.2, 53.1, 47.8, 46.1, 44.3, 32.8, 24.3, 13.9. HPLC analysis of the Marfey's derivative of 5 indicated >99.5 % ee. Sample preparation for Marfey's derivatization: 0.5 mg tartrate salt, 0.5 mg Marfey's reagent {N-(2,4-Dinitro-5-fluorophenyl)-L-alaninamide}, 50 μL of 6M NaHCO$_3$ and 0.5 mL acetone were combined. The mixture was heated at 55° C. (4–5 min.) until it turned red in color from light yellow and made up to 1 mL with 1:1 MeCN and H$_2$O. HPLC conditions: B-03-5 YMC Basic (S-5 micron) 250×4.6 mm column, isocratic elution over 10 min (42/58) MeCN/0.025% H$_3$PO$_4$, then gradient elution over 5 min (42/58→62/38) MeCN/0.025% H$_3$PO$_4$, then isocratic elution over 15 min (62/38) MeCN/0.025% H$_3$PO$_4$, 1.0 mL/min flow at 25° C. with detection at 220 nm.

| Elution Schedule retention time (min.) | identity |
| --- | --- |
| 4.0 | benzyl ethyl nipecotate 5 |
| 6.2 | Marfey's reagent |
| 19.5 | Marfey's derivatized (S)-5 |
| 19.9 | Marfey's derivatized (R)-5 |

EXAMPLE 2

(S)-3-Carbethoxy-3-benzylpiperidine

Step A: (S)-3-Carbethoxy-3-benzyl-2-piperidone (3)

A solution of carboxylic acid monoester 2 (5.0 g, 13.2 mmol) in CH$_2$Cl$_2$ (50 mL) in a 250 mL flask was cooled to 0° C. The HCl gas was passed in until 50 mmol absorbed by the mixture. The reaction mixture was stirred for 2 h and was found to be complete by HPLC analysis. The volatiles were removed from the mixture by a stream of N$_2$. The HCl salt 6 was redissolved in 50 mL of CH$_2$Cl$_2$. DIEA (5.05 mL, 28.99 mmol) was added to the mixture and stirred for 5–6 minutes (pH of the mixture was at 9.5). 2-Chloro-1-methyl pyridinium iodide (5.05 g, 19.8 mmol) was added and the mixture was aged for 30 minutes. After 1 h, HPLC analysis indicated <0.2 mol% of 2 remaining, indicating complete reaction. HPLC conditions: B-03-5 YMC Basic (S-5 micron) 250×4.6 mm column, isocratic elution over 10 min (42/58) MeCN/0.025% H$_3$PO$_4$, then gradient elution over 5 min 4(2/58→62/38) MeCN/0.025% H$_3$PO$_4$, then isocratic elution over 15 min (62/38) MeCN/0.025% H$_3$PO$_4$, 1.0 mL/min flow at 25° C. with detection at 220 nm, retention times:

| Elution Schedule retention time (min.) | identity |
| --- | --- |
| 3.5 | HCl salt 6 |
| 7.35 | lactam 3 |
| 16.9 | carboxylic acid monoester 2 |

EtOAc (150 mL) and water (50 mL) were added to the mixture. The aqueous phase was separated and the organic phase was washed with 15 mL of 2N HCl diluted to 60 mL with water and then with 50 mL of saturated NaHCO$_3$ solution. Finally, the organic phase was washed with 50 mL of 10% brine and dried over Na$_2$SO$_4$. The reaction mixture was concentrated to give lactam 3 (80% assay yield by HPLC analysis). (identical to previously prepared material). Chiral supercritical phase HPLC indicated 3 to be >99.5 % ee HPLC conditions: Sumichiral AG OA3200 250×4.6 mm column, isocratic elution, 16% MeOH in supercritical CO$_2$ at 300 bar, 2.0 mL/min flow at 35° C. with detection at 210 nm. Retention times: (R)–3=2.35 min, (S)–3=2.87 min.

Step B: (S)-3-Carbethoxy-3-benzyl-N-Boc-2-piperidone (7)

To a solution of lactam 3 (2.30 g, 8.80 mmol) in toluene (25 mL) was added DMAP (1.61 g, 13.2 mmol) followed by Boc$_2$O (2.31 g, 10.6 mmol). The resulting mixture was heated to 60° C. and was stirred for an hour. The reaction was complete (<0.1% of 3) by HPLC analysis. HPLC conditions: B-03-5 YMC Basic (S-5 micron) 250×4.6 mm column, isocratic elution over 10 min (42/58) MeCN/0.025% H$_3$PO$_4$, then gradient elution over 5 min (42/58→62/38) MeCN/0.025% H$_3$PO$_4$, then isocratic elution over 15 min (62/38) MeCN/0.025% H$_3$PO$_4$, 1.0 mL/min flow at 25° C. with detection at 220 nm.

| Elution Schedule retention time (min.) | identity |
| --- | --- |
| 7.35 | lactam 3 |
| 21.5 | N-Boc-lactam 7 |

The mixture was diluted with 50 mL of toluene and was washed twice with saturated NaH$_2$PO$_4$ solution (1×50 mL, 1×20 mL). Finally, the mixture was washed with brine (50 mL) and dried over Na$_2$SO$_4$. The mixture was concentrated to an oily residue affording 7 (93% yield, >95 A % purity by HPLC analysis, same conditions as above). $^{13}$C NMR (62.9 MHz, CDCl$_3$) δ 172.0, 170.3, 152.8, 136.1, 130.7, 128.1, 35 126.9, 82.9, 61.7, 57.7, 45.6, 41.6, 29.0, 28.0, 20.0, 14.0.

Step C: S-3-Carbethoxy-3-benzyl-2-hydroxy-N-Boc-piperidine (8)

The N-Boc-lactam 7 (1.22 g, 3.37 mmol) was dissolved in THF (5 mL) and was cooled to −10° C. in an ice-acetone bath. Super hydride™ (1.0M, 4.1 mL, 4.05 mmol) was added slowly to the reaction mixture through a syringe. The reaction was aged for 2 h and had reached completion (<0.1 mol % of 7 remained) by HPLC analysis: B-03-5 YMC Basic (S-5 micron) 250×4.6 mm column, isocratic elution over 10 min (42/58) MeCN/0.025% H$_3$PO$_4$, then gradient elution over 5 min (42/58→62/38) MeCN/0.025% H$_3$PO$_4$, then isocratic elution over 15 min (62/38) MeCN/0.025% H$_3$PO$_4$, 1.0 mL/min flow at 25° C. with detection at 220 nm.

| Elution Schedule retention time (min.) | identity |
|---|---|
| 20.0 | N-Boc-aminal 8 |
| 21.5 | N-Boc-lactam 7 |

Any remaining hydride was quenched by adding 15 mL of cold water to the reaction mixture. The product was extracted in 40 mL of EtOAc, and concentrated to a residue that was >90 A % purity by HPLC analysis (same conditions as above). $^{13}$C NMR indicated 8 to be a ca 3:2 mixture of diastereomers. $^{13}$C NMR (62.9 MHz, CDC13) δ 173.1, 171.4, 154.9, 136.8, 136.7, 129.9, 129.8, 128.3, 128.1, 126.8, 126.7, 80.8, 80.2, 60.7, 60.4, 52.8, 51.8, 43.2, 38.0, 28.5, 28.4, 26.8, 22.3, 21.2, 20.1, 14.3, 14.1, 14.0.

Step D: S-3-Carbethoxy-3-benzyl-N-Boc-piperidine (9)

A solution of N-Boc-aminal 8 (580 mg, 1.59 mmol) and triethylsilane (255 μL, 1.59 mmol) in CH$_2$Cl$_2$ (8 mL) was cooled to −78° C. and boron trifluoride etherate (197 μL, 1.59 mmol) was then added dropwise under a nitrogen atmosphere. After 30 min, the remaining 255 μL of triethylsilane and 197 μL of borontrifluoride were added. The resulting mixture was stirred for 2 h at −78° C. and was found complete by HPLC analysis: B-03-5 YMC Basic (S-5 micron) 250×4.6 mm column, isocratic elution over 10 min (42/58) MeCN/0.025% H$_3$PO$_4$, then gradient elution over 5 min (42/58→62/38) MeCN/0.025% H$_3$PO$_4$, then isocratic elution over 15 min (62/38) MeCN/0.025% H$_3$PO$_4$, 1.0 mL/min flow at 25° C. with detection at 220 nm. This mixture was used crude in the next step.

| Elution Schedule retention time (min.) | identity |
|---|---|
| 4.0 | piperidine 5 |
| 20.0 | N-Boc-aminal 8 |
| 25.4 | N-Boc-piperidine 9 |

Step E: (S)-3-carbethoxy-3-benzyl piperidine (5)

Piperidine 9 was deprotected by passing HCl gas through the reaction mixture from the previous step until 87 mg had been absorbed. The resulting amine HCl salt was extracted into water (50 mL). MTBE (50 mL) was added to the mixture and the organic phase was separated. NaOH (5N, 7 mL) was added to the aqueous phase for basification of the HCl salt (to pH 11.5). The free amine was extracted twice with EtOAc (1×40 mL, 1×20 mL) and dried over Na$_2$SO$_4$. The solution was evaporated to afford 363 mg of 5 as a light yellow oil (92.4 wt % pure by HPLC analysis, 85% yield). HPLC analysis of the Marfey's derivative of 5 indicated >99.5 % ee. (Same conditions as described previously).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A process for the preparation of a compound of the structural formula 5:

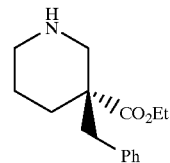

which comprises the steps of:

a) treating a compound of structural formula 1:

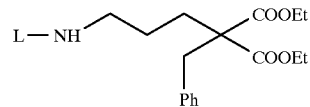

wherein L is an amino protecting group, with an esterase to give a compound of structural formula 2:

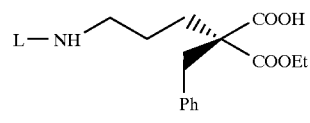

b) cyclizing the compound of structural formula 2 to give a compound of structural formula 3:

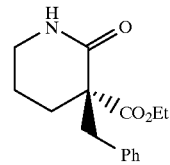

c) reducing the carbonyl of the compound of structural formula 3 to give the compound of structural formula 5.

2. The process of claim 1 wherein the esterase is a liver esterase.

3. The process of claim 1 wherein the esterase is a pig (porcine) liver esterase.

4. The process of claim 1 wherein the esterase is a pig rabbit liver esterase.

5. The process of claim 1 wherein the treatment of the compound of formula 1 with an esterase is conducted in the presence of a gum selected from the group consisting of: xanthan gum, locust bean gum, arabic gum, tragacanth gum, guar gum, elemi gum, and karaya gum.

6. The process of claim 2 wherein the treatment of the compound of formula 1 with a liver esterase is conducted in the presence of a gum selected from the group consisting of: xanthan gum, tragacanth gum, guar gum, elemi gum, and karaya gum.

7. The process of claim 2 wherein the treatment of the compound of formula 1 with an esterase is conducted in the presence of a gum selected from the group consisting of: xanthan gum, tragacanth gum, and guar gum.

8. The process of claim 2 wherein the treatment of the compound of formula 1 with an esterase is conducted in the presence of xanthan gum.

9. A process for the preparation of a compound of structural formula 5:

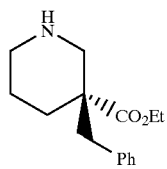

5 which comprises the steps of:

a) treating the compound of structural formula I:

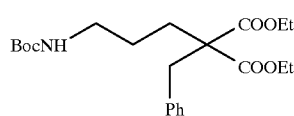

1 with a liver esterase to give the compound of structural formula 2:

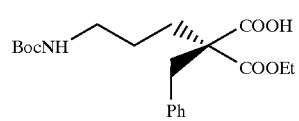

2 b) deprotecting the compound of structural formula 2 with trifluoracetic acid or hydrochloric acid followed by cyclization with dicyclohexylcarbodiimide and 1-hydroxybenzotriazole or 2-chloro-N-methylpyridinium iodide to give the compound of structural formula 3:

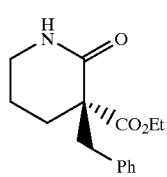

3 c) treating the compound of structural formula 3 with Lawesson's reagent to give the compound of structural formula 4:

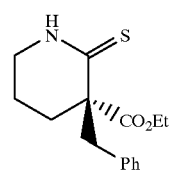

4 d) treating the compound of structural formula 4 with Raney nickel to give the compound of structural formula 5.

10. The process of claim 9 wherein the esterase is a liver esterase.

11. The process of claim 9 wherein the esterase is a pig (porcine) liver esterase.

12. The process of claim 9 wherein the esterase is a pig rabbit liver esterase.

13. The process of claim 9 wherein the treatment of the compound of formula 1 with an esterase is conducted in the presence of a gum selected from the group consisting of: xanthan gum, locust bean gum, arabic gum, tragacanth gum, guar gum, elemi gum, and karaya gum.

14. The process of claim 10 wherein the treatment of the compound of formula 1 with a liver esterase is conducted in the presence of a gum selected from the group consisting of: xanthan gum, tragacanth gum, guar gum, elemi gum, and karaya gum.

15. The process of claim 10 wherein the treatment of the compound of formula 1 with an esterase is conducted in the presence of a gum selected from the group consisting of: xanthan gum, tragacanth gum, and guar gum.

16. The process of claim 10 wherein the treatment of the compound of formula 1 with an esterase is conducted in the presence of xanthan gum.

17. The process of claim 10 wherein the deprotection of the compound of structural formula 2 is conducted with trifluoracetic acid.

18. The process of claim 10 wherein the cyclization is conducted with dicyclohexylcarbodiimide and 1-hydroxybenzotriazole.

19. A process for the preparation of a compound of structural formula 5:

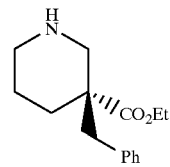

5 which comprises the steps of:

a) treating the compound of structural formula I:

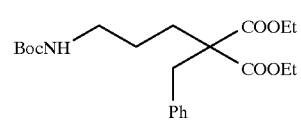

1 with a liver esterase to give the compound of structural formula 2:

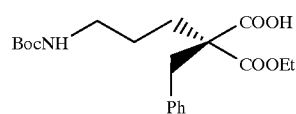

b) deprotecting the compound of structural formula 2 with hydrochloric acid, followed by cyclization with 2-chloro-N-methylpyridinium iodide to give the compound of structural formula 3:

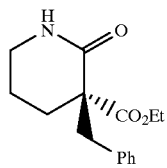

c) activating the compound of structural formula 3 as its Boc-derivative followed by reducing the carbonyl by sequential treatment with lithium triethyl borane (LiEt$_3$BH) and diethylsilane/boron trifluoride etherate and hydrolyzing of the Boc group with an acid to give the compound of structural formula 5.

20. The process of claim 19 wherein the esterase is a liver esterase.

21. The process of claim 19 wherein the esterase is a pig (porcine) liver esterase.

22. The process of claim 19 wherein the esterase is a pig rabbit liver esterase.

23. The process of claim 19 wherein the treatment of the compound of formula 1 with an esterase is conducted in the presence of a gum selected from the group consisting of: xanthan gum, locust bean gum, arabic gum, tragacanth gum, guar gum, elemi gum, and karaya gum.

24. The process of claim 20 wherein the treatment of the compound of formula 1 with a liver esterase is conducted in the presence of a gum selected from the group consisting of: xanthan gum, tragacanth gum, guar gum, elemi gum, and karaya gum.

25. The process of claim 20 wherein the treatment of the compound of formula 1 with an esterase is conducted in the presence of a gum selected from the group consisting of: xanthan gum, tragacanth gum, and guar gum.

26. The process of claim 20 wherein the treatment of the compound of formula 1 with an esterase is conducted in the presence of xanthan gum.

* * * * *